(12) United States Patent
Palma

(10) Patent No.: US 10,157,460 B2
(45) Date of Patent: Dec. 18, 2018

(54) INTERPOLATED TOMOSYNTHESIS PROJECTION IMAGES

(71) Applicant: General Electric Company, Schenectady, NY (US)

(72) Inventor: Giovanni John Jacques Palma, Buc (FR)

(73) Assignee: General Electric Company, Schenectady, NY (US)

(*) Notice: Subject to any disclaimer, the term of this patent is extended or adjusted under 35 U.S.C. 154(b) by 52 days.

(21) Appl. No.: 15/334,025

(22) Filed: Oct. 25, 2016

(65) Prior Publication Data

US 2018/0114312 A1    Apr. 26, 2018

(51) Int. Cl.
| | |
|---|---|
| *G06K 9/00* | (2006.01) |
| *G06T 7/00* | (2017.01) |
| *G06T 11/00* | (2006.01) |
| *G06T 15/08* | (2011.01) |

(Continued)

(52) U.S. Cl.
CPC ............ *G06T 7/0012* (2013.01); *A61B 6/025* (2013.01); *A61B 6/466* (2013.01); *A61B 6/502* (2013.01); *G06T 7/0042* (2013.01); *G06T 11/003* (2013.01); *G06T 11/006* (2013.01); *G06T 15/08* (2013.01); *G06T 2207/10116* (2013.01); *G06T 2211/436* (2013.01)

(58) Field of Classification Search
CPC ......... A61B 6/025; A61B 6/466; A61B 6/502; G06T 11/003; G06T 15/08; G06T 2207/10116; G06T 7/0012; G06T 7/0042; G06T 11/006; G06T 2211/436
See application file for complete search history.

(56) References Cited

U.S. PATENT DOCUMENTS

| | | |
|---|---|---|
| 6,196,715 B1 | 3/2001 | Nambu et al. |
| 7,881,428 B2 | 2/2011 | Jing et al. |
| 8,452,379 B2 | 5/2013 | Defreitas et al. |
| | (Continued) | |

FOREIGN PATENT DOCUMENTS

| | | |
|---|---|---|
| EP | 1351192 A1 | 10/2003 |
| EP | 1792569 A2 | 6/2007 |
| | (Continued) | |

OTHER PUBLICATIONS

Extended European Search Report and Opinion issued in connection with corresponding EP Application No. 16204123.0 dated Aug. 8, 2017.

(Continued)

*Primary Examiner* — Tom Y Lu
(74) *Attorney, Agent, or Firm* — Andrus Intellectual Property Law, LLP

(57) ABSTRACT

Systems and methods of medical imaging includes acquiring a plurality of projection images. A first projection image and a second projection image from the plurality of projection images are selected that are adjacent to a received focal point. A first set of object locations in the first projection image and a second set of object locations in the second projection image are identified that contribute to a pixel of the synthetic projection image. A value for the pixel of the synthetic projection image is calculated from the pixels of the first set of object locations and the pixels of the second set of object locations. The synthetic projection image is created with the calculated value.

22 Claims, 6 Drawing Sheets

(51) Int. Cl.
    *A61B 6/00*         (2006.01)
    *A61B 6/02*         (2006.01)

(56) References Cited

U.S. PATENT DOCUMENTS

| | | |
|---|---|---|
| 8,565,374 B2 | 10/2013 | Defreitas et al. |
| 8,824,761 B2 | 9/2014 | Palma et al. |
| 9,724,047 B2 * | 8/2017 | Hornig .................. A61B 6/025 |
| 2003/0072478 A1 | 4/2003 | Claus et al. |
| 2005/0133708 A1 | 6/2005 | Eberhard et al. |
| 2008/0045833 A1 | 2/2008 | Defreitas et al. |
| 2008/0267476 A1 | 10/2008 | Langan et al. |
| 2011/0150178 A1 | 6/2011 | Bernard et al. |
| 2012/0121064 A1 | 5/2012 | Bernard |

FOREIGN PATENT DOCUMENTS

| | | |
|---|---|---|
| FR | 2905256 A | 3/2008 |
| GB | 2533801 A | 7/2016 |
| JP | 2015506794 A | 3/2015 |
| WO | 01/80184 A1 | 10/2001 |

OTHER PUBLICATIONS

Kalke et al., "Sinogram Interpolation Method for Sparse-Angle Tomography", Applied Mathematics, Feb. 2014, vol. 5, pp. 423-441.
GE Healthcare Brochure—SenoClaire 3D Breast Tomosynthesis, 2014.

\* cited by examiner

INTERPOLATED TOMOSYNTHESIS PROJECTION IMAGES

BACKGROUND

The present disclosure is related to the field of tomography. More specifically, the present disclosure is related to the field of digital breast tomography (DBT), the interpolation of synthetic projection images from DBT data, and the use of such synthetic projection images.

For the diagnosis of breast cancer, radiology is generally used to obtain an image of the inside of the breast. A two-dimensional (2D) radiological image shows a projection of a tissue matrix, e.g. a breast for breast cancer diagnosis, onto a plane formed by a detector, from a radiation source. The radiological image is generally obtained by placing the object of interest between the X-ray emitting source and the X-ray detector, so that the rays reach the detector after passing through the object. The radiological image is then created from data provided by the detector, and represents the tissue matrix projected onto the detector in the direction of the X-rays.

In such a radiological image, an experienced practitioner can distinguish radiological signs indicating a potential problem, e.g. micro-calcifications, lesions, or other opacities in the case of mammography. However, a radiological image is derived from a two-dimensional projection of a three-dimensional tissue matrix. Tissue superposition may mask radiological signs such as lesions, and under no circumstance is the true position of the radiological signs inside the object of interest known; the practitioner having no information on the position of the radiological signs in the direction of projection.

Tomosynthesis has recently been developed to address these issues; it allows a three-dimensional (3D) representation of an object of interest to be obtained in the form of a series of successive slices. These slices are reconstructed from projections of the object of interest at different angles. For this purpose, the object of interest is generally placed between an X-ray emitting source and an X-ray detector. The source and/or the detector are movable, which means that the projection direction of the object of interest onto the detector can be varied. In this manner, several projections of the object of interest are obtained at different angles, from which a 3D representation of the object of interest can be reconstructed.

For each tomosynthesis projection image, the radiation doses of the X-rays are naturally less than those used for standard mammography. For example, by noting as D the radiation dose of standard mammography, and as N the number of projections used for tomosynthesis, the radiation dose used for each projection is of the order of D/N. While operating within this general constraint on tomosynthesis imaging, a tradeoff must be made between the number of tomosynthesis projection images and the radiation does used to acquire each individual projection image. Radiation dose is generally associated with higher X-ray image quality through improved contrast, up to saturation levels. However, greater numbers of projection images can improve tomographic 3D reconstructions, or rather, 3D reconstructions from limited number of projection images are subject to exhibit artifacts known as "streaking." In reality, all iterative reconstruction techniques produce a "streak" artifact for each projection image used in the reconstruction. However, the intensity of the artifact diminishes with each additional projection image used in the reconstruction.

Additionally, techniques are known for creating synthetic 2D mammography images by reconstructing a 3D volume from the tomosynthesis projection images and then using that 3D reconstruction to enhance one of the acquired tomosynthesis projection images into the synthetic 2D mammography image. However, those techniques are limited to producing synthetic mammography images at the positions from which the original tomosynthesis projection images were acquired.

BRIEF DISCLOSURE

An exemplary embodiment of a system for medical imaging includes an acquisition unit and an imaging processing unit. The acquisition unit includes a radiation source configured to emit x-rays and an x-ray detector configured to receive x-rays that pass through an object to be imaged and produced numerical values representative of the received x-rays. The acquisition unit is moveable about the object to be imaged to acquire a plurality of projection images. Each projection image is acquired at a different angle relative to the object to be imaged. The image processing unit receives an input of a focal point for a synthetic projection image. The image processing unit selects a first projection image and a second projection image adjacent to the focal point from the plurality of projection images. For each pixel of the synthetic projection image, the image processing unit identifies a first set of object locations in the first projection image and a second set of object locations in the second projection image that contribute to a pixel of the synthetic projection image. For each pixel of the synthetic projection image, the image processing unit further calculates a value for the pixel of the synthetic projection image from the pixels of the first set of object locations and the second set of object locations. The image processing unit creates a synthetic projection image from the calculated values of each pixel of the synthetic projection image.

An exemplary embodiment of a method of medical imaging includes acquiring a plurality of projection images with an acquisition unit. An input of the focal point for a synthetic projection image is received. A first projection image and a second projection image are selected from the plurality of projection images that are adjacent the focal point. A first set of object locations that contribute to a pixel of the synthetic projection image are identified in the first projection image. A second set of object locations that contribute to the pixel of the synthetic projection image are identified in the second projection image. A value for the pixel of the synthetic projection image is calculated from the pixels of the first set of object locations and the second set of object locations. The synthetic projection image is created from the calculated value of the pixel of the synthetic projection image.

In a further exemplary embodiment a 3D volume is reconstructed from a combination of the plurality of projection images acquired with the acquisition unit and at least one synthetic projection image. A plurality of synthetic projection images can be created from a plurality of received focal points, at least one focal point of the plurality of received focal points being located between each of the plurality of projection images acquired with the acquisition unit. The 3D volume can be reconstructed using the plurality of synthetic projection images in combination with the plurality of projection images acquired with the acquisition unit.

A still further exemplary embodiment may additionally include a synthetic two-dimensional (2D) image from the received focal point for the synthetic projection image. A 3D volume may be reconstructed from at least the plurality of projection images acquired with the acquisition unit. An intermediate 2D image can be created from the received focal point for the synthetic projection image from the reconstructed 3D volume. The intermediate 2D image may be combined with the synthetic projection image to create the synthetic 2D image.

BRIEF DESCRIPTION OF THE DRAWINGS

The accompanying drawings, which are incorporated in and constitute a part of the specification, illustrated one or more non-limiting embodiments and, together with the description, explain these embodiments.

DETAILED DISCLOSURE

Figure 1:
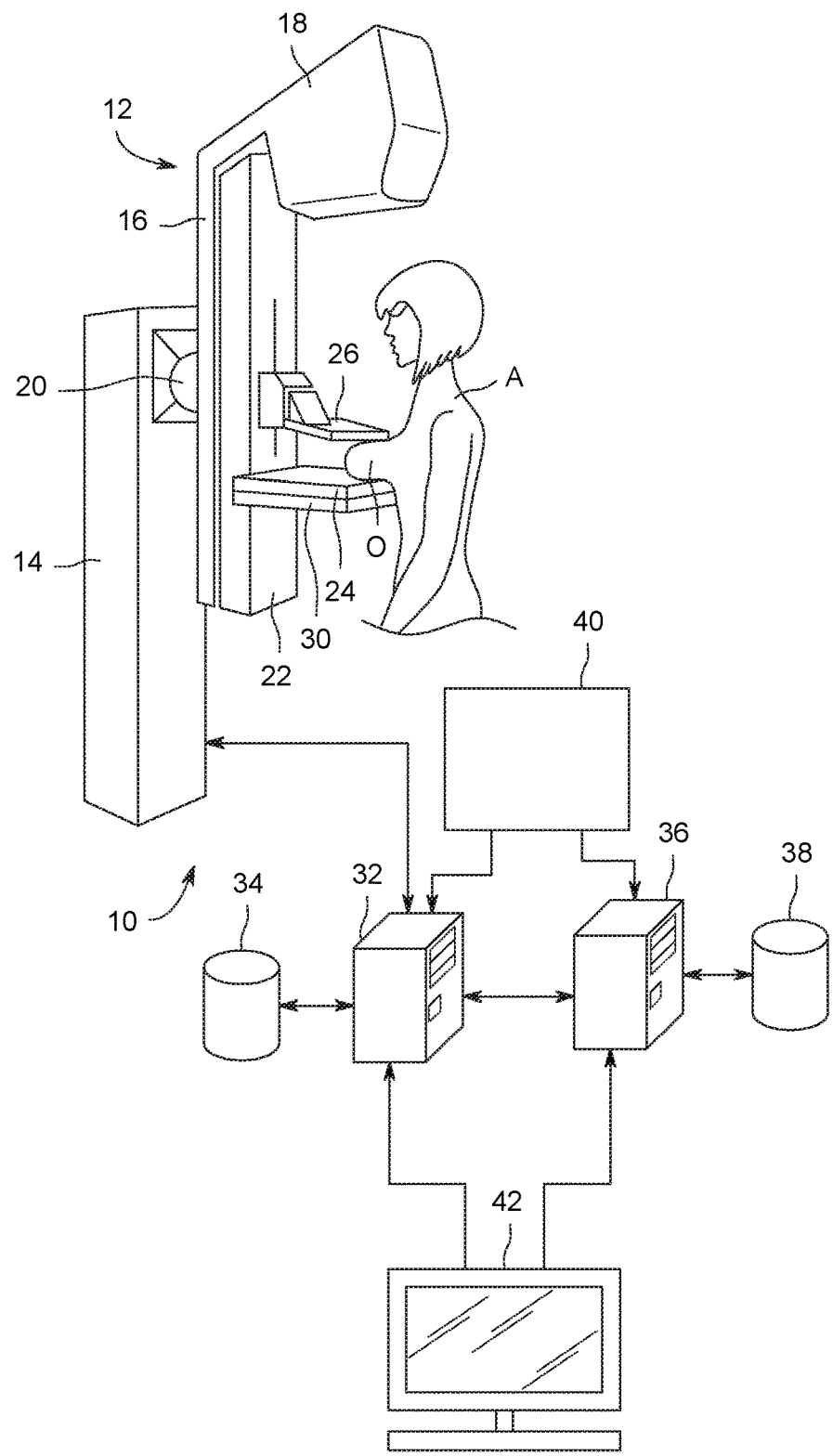
FIG. 1 schematically illustrates a medical imaging system used to acquire medical images, coupled with a computing system to implement the method.

FIG. 1 depicts an exemplary embodiment of a medical imaging system 10. The medical imaging system 10 exemplarily operates in the manners as described herein in order to create synthetic projection images which may be used to create improved three-dimensional reconstruction images and synthetic two-dimensional images. The medical imaging system 10, as described in further detail herein enables the acquisition of 2D projection images of a tissue matrix of an organ O, exemplarily a breast of a patient A. The medical imaging system 10 processes the 2D projection images as described in further detail herein to create a 3D reconstruction of the tissue matrix of the organ O.

The imaging system 10 includes an acquisition unit 12 which operates to acquire the 2D projection images. The acquisition unit 12 exemplarily includes a vertical stand 14 and a positioning arm 16 which includes a radiation source 18 e.g. an X-ray emitter. The positioning arm 16 is exemplarily rotationally joined to the vertical stand 14 about a rotation shaft 20. The vertical stand 14 is fixed. Therefore, by moving the positioning arm 16, the radiation source 18 can be positioned at various orientations about the rotation shaft 20.

The acquisition unit 12 further includes a support arm 22. The support arm exemplarily includes a detector support 24 and a compression support 26. The detector support 24 is configured to support the organ O from below and exemplarily includes an X-ray detector as described in further detail herein. The compression support 26 is generally parallel to the detector support 24 and is generally translatable to various positions along a translation rail 28 relative to the detector support. The compression support exemplarily moves towards the detector support 24 to compress the breast O placed between the two supports for medical imaging. Compression of the breast between the detector support 24 and the compression support 26 keeps the breast O immobile during the acquisition of medical images and improves uniformity of the tissue matrix which improves imaging.

The detector support 24 further includes an anti-diffusion grid 30 which exemplarily includes a plurality of opaque components arranged in parallel to one another, in a direction parallel to the motion of the positioning arm and operates to limit the impact and spread of emitted X-rays within the body of the patient A. The positioning arm 16 and the support arm 22 may be joined to one another or may be separate components, allowing their rotation relative to each other about the rotation shaft 20. In still further embodiments, the detector support 24 may be translatable and/or rotatable in order to accommodate a height of the patient. In still further embodiments, while not depicted, the acquisition unit 12 may include a lower support that supports the breast O while the detector 24 is connected to the positioning arm 16 for coordinated movement between the detector 24 and the radiation source 18. In other embodiments, the X-ray emitter within the radiation source 18 may correspondingly adjust the X-ray beam emitted from the radiation source 18 such as to maintain the breast O in the X-ray beam while keeping the X-ray beam in alignment with the detector 24 to maximize the part of the X-ray radiation emitted by the radiation source 18 that impinges upon the detector 24. The detector 24 may include a semi conductor image sensor containing cesium iodide phosphor for example (scintillator) on a transistor/photodiode array in amorphous silicon. Other suitable detectors are: a CCD sensor or a direct digital detector which directly converts X-rays into digital signals. While the detector 24 illustrated in FIG. 1 is planar and defines a planar image surface, other geometries will be recognized as being suitable depending upon the acquisition unit 12, including, but not limited to digital X-ray detectors of curved shape forming a curved image surface.

The detector exemplarily located within the detector support 24 is exemplarily an array formed by a plurality of detector rows (not shown) including a plurality of detector elements which together sense the projected X-rays that pass through the object O. Each detector element of the detector array produces an electrical signal that represents the intensity of an impinging X-ray beam and hence the attenuation of the beam as it passes through the object O. While the Figures as shown and described herein may only show a single row of a detector ray or detector elements, it will be recognized that the detector includes a plurality of parallel rows of detector elements so that projection data corresponding to a plurality of quasi-parallel or parallel slices can be acquired simultaneously during a scan. The control unit 32 provides power and timing signals to both the X-ray source 18 and the detector such that a data acquisition system of the control unit 32 samples the X-ray data from the detector elements and converts the data to digital signals for subsequent processing.

The imaging system 10 further includes a control unit 32 connected to the acquisition unit 12 either by wired or wireless communicative connections. The control unit 32 sends electric control signals to the acquisition 12 to set several parameters such as the radiation dose to be emitted, the angle and/or position of the positioning arm 16, the angle and/or positioning of the support arm 22, and the angle and/or position of the detector support 24 and/or compression support 26. The control unit 32 may include computer memory or a reader device for reading data and/or computer code stored on computer memory, for example magnetic or solid state memory devices, or other removable computer readable media which may be read by the control unit 32 to access computer readable code with instructions of the methods as described herein. The control unit 32 may be implemented on one or more computer processors that may further include a communicative connection, wither wired or wirelessly, to a memory unit 34 which may be a ROM/RAM memory of the control unit 32, a USB flash drive, memory card, or computer memory of a networked server. The control unit 32 operates to record parameters and/or required images in the computer memory 34.

The imaging system 10 further includes an image processing unit 36 which may be implemented as part of the same processor or processors as the control unit 32, or may be implemented on one or more different processors yet communicatively connected to the control unit 32. The image processing unit 36 receives the medical images acquired by the acquisition unit 12 under the operation of the control unit 32 and processes the acquired medical images in the manners as described herein through execution of computer readable code stored on a non-transient computer readable medium communicatively connected to the image processing unit 36 upon which such computer readable code is stored. Execution of the computer readable code by the image processing unit causes the image processing unit to carry out the functions and operations as described in further detail herein. The image processing unit 36 is further communicatively connected to computer memory 38 to store the processed medical images and further medical images as generated through the operation of the image processing unit 36. In embodiments, the computer memory 38 may be embodied as computer memory 34, or a different computer memory.

The control unit 32 and the image processing unit 36 are both connected to an input device 40 which may be any of a variety of input devices, including, but not limited to keyboard, push buttons, touch screen displays with graphical user interfaces (GUI), or any of a combination of the above or other input devices as will be recognized by one of ordinary skill in the art.

The input device 40 is operated by a clinician or technician to input control commands and/or processing commands and to interact with the medical images as generated by the imaging system 10. In an exemplary embodiment, the input device 40 may be a part of or associated with a graphical display 42 to which the control unit 32 and the image processing unit 36 are connected. The graphical display 42 is operated to present one or more graphical user interfaces (GUI) to visually present information regarding the acquisition of medical images by the acquisition unit 12 and/or to present the acquired medical images or the medical images as generated by the image processing unit 36 as will be described in further detail herein. It will also be recognized that while graphical display 42 is depicted as a single graphical display, that multiple graphical displays and/or graphical displays located at different locations, including, but not limited to mobile devices may be used in implementing various embodiments of the systems and methods as disclosed herein.

Figure 2:
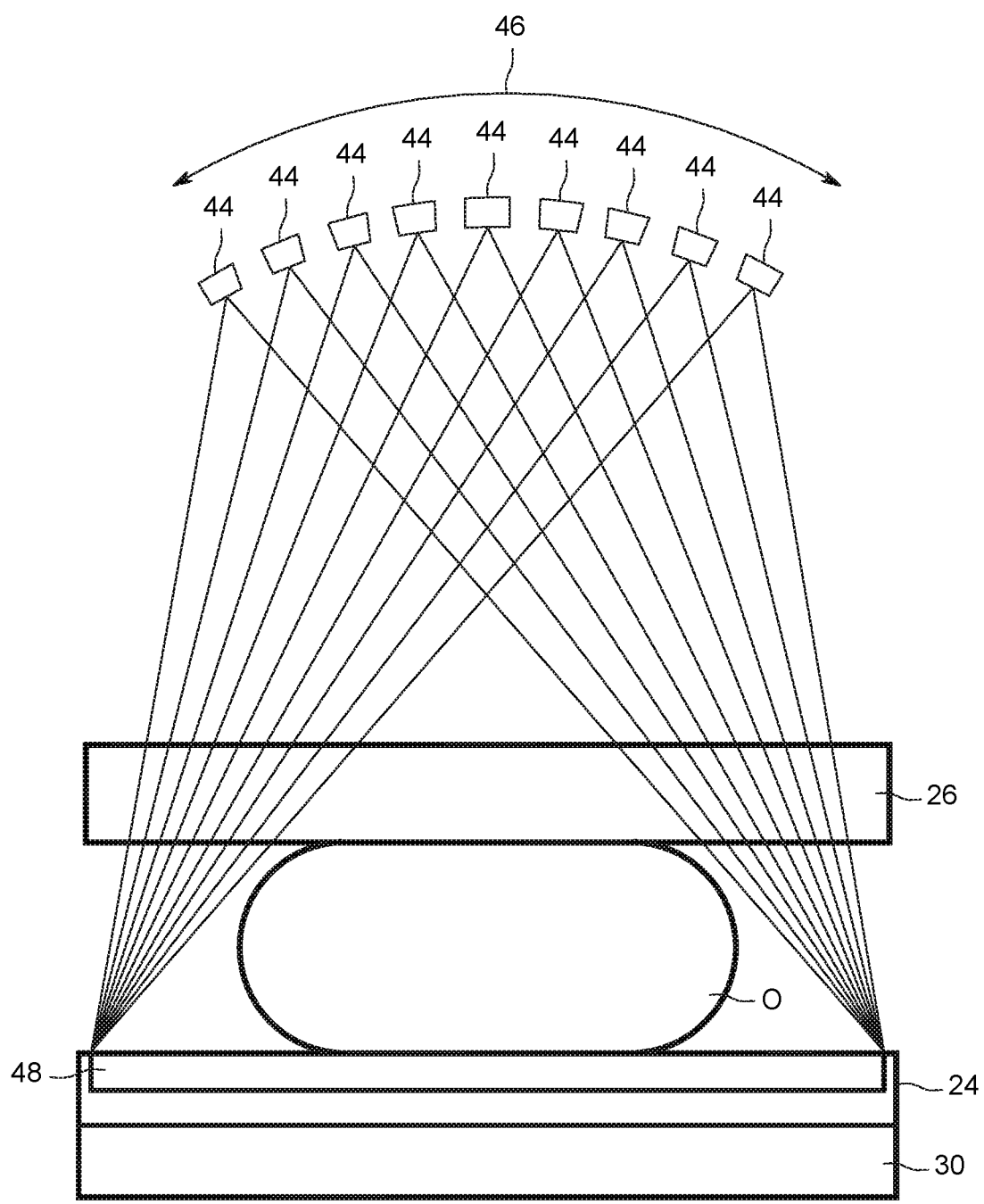
FIG. 2 illustrates acquisition of a plurality of projection images.

FIG. 2 diagrammatically depicts acquisition of a plurality of tomographic (e.g. digital breast tomography (DBT) projection images. In FIG. 2 a patient's breast O is compressed between the compression support 26 and the detector support 24. As described above, an anti-diffusion grid 30 is located below the detector 24 to limit the effects of X-ray radiation on the rest of the patient's body. FIG. 2 depicts an X-ray emitter 44 (which is exemplarily located within the radiation source 18 of the acquisition unit 12 as shown in FIG. 1) located at a variety of positions relative to the patient's breast O. The control unit 32 may provide positioning signals to the positioning arm (not depicted) to adjust the position of the X-ray emitter 44. The control unit may further provide control instruction to the radiation source to control the shape and/or strength of the X-ray beam emitted from the X-ray emitter 44 at each of the plurality of positions. In an exemplary embodiment, the emitted X-ray beams may be shaped to adjust for a stationary detector support 24 such as to maximize the X-ray beam that impinges on both the breast O and the detector support 24. The detector contained in the detector support 24 detects the radiation passing through the breast O, and the control unit 32 stores the image read on the detector in the memory unit 34. In embodiments, the control unit further stores the position of the X-ray emitter 44 used to acquire each of the projection images and/or the position of the detector (e.g. via the position of the detector support 24 in the embodiment depicted). This acquisition operation is repeated for several positions of the X-ray emitter 44 about the breast O. In an exemplary embodiment, the positions of the X-ray emitter are evenly spread across an acquisition geometry 46. In an exemplary embodiment, the acquisition geometry 46 may exemplarily be an arc, linear, or any other (including more complex) geometry. The acquisition geometry 46 may exemplarily be 20° of arc, 25° of arc, 30° of arc, 40° of arc, or 60° of arc. It will be understood that these sizes of the acquisition geometry 46 are exemplary in nature and that other arc sizes may be used as will be recognized by a person of ordinary skill in the art in view of the present disclosure.

In an exemplary embodiment, the positions of the X-ray emitter are evenly spaced across the acquisition geometry 46. In the exemplary embodiment depicted, nine projection images each taken at a different position of the X-ray emitter 44 are acquired by the acquisition unit. As noted above, the radiation dose for each of the tomographic projection images will typically be one ninth of a standard radiation dose of a full field digital mammogram (FFDM) image. In the exemplary embodiment wherein nine projection images are acquired, one of the projection images will typically be acquired from a position normal to the center of the detector in the a spline detector support representative of zero degrees of arc along the acquisition geometry 46. The other X-ray emitter positions may be evenly spaced in either direction along the imaging arc from this center image. It will be recognized that in still further embodiments, the detector and detector support 24 may be rotated and the center image position of the X-ray emitter as well as the acquisition geometry 46 may be rotated to maintain this relationship between the X-ray emitter positions along the acquisition geometry 46 and the detector in the detector support 24 relative to the patient's breast O.

Figure 4:
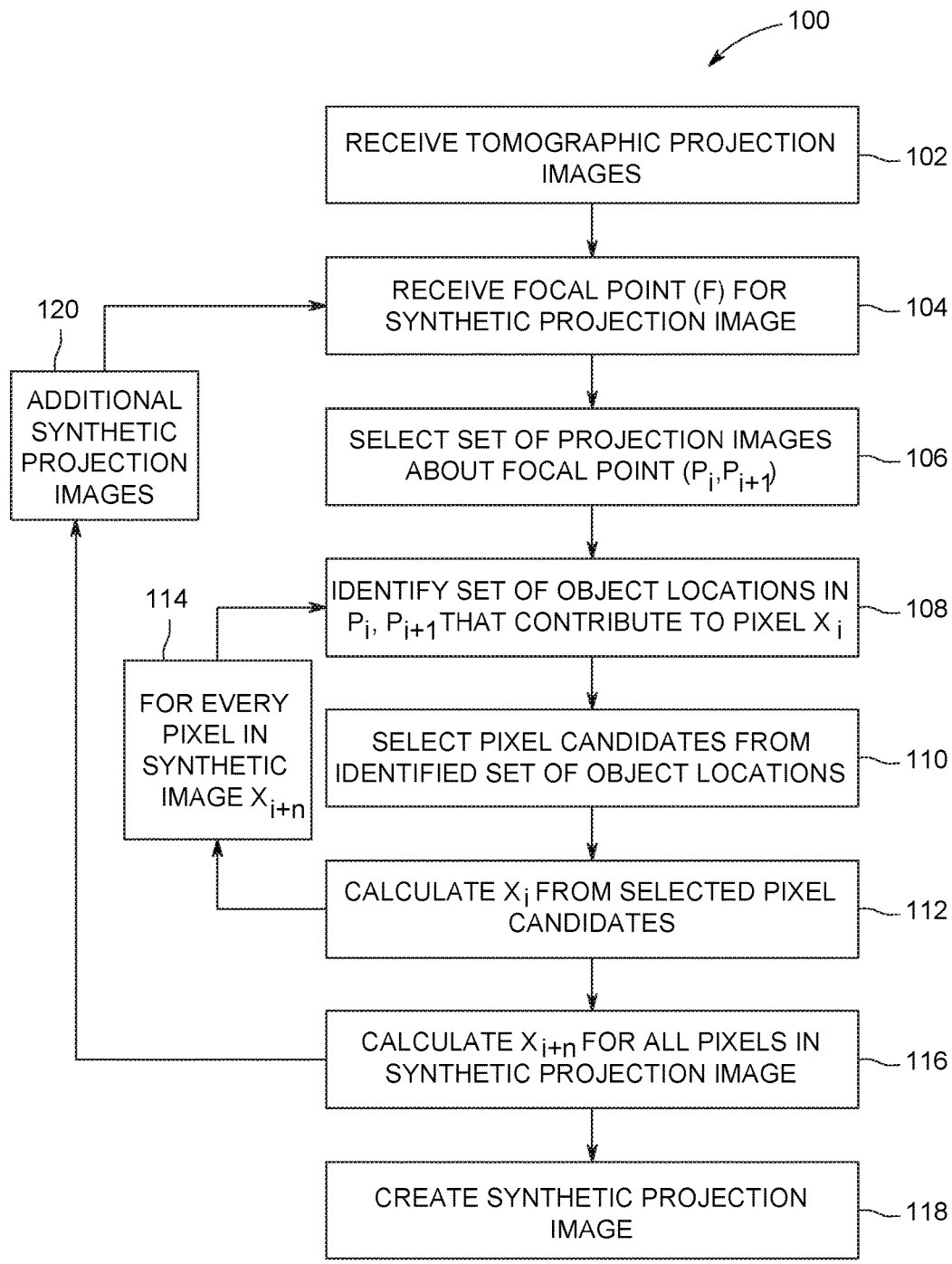
FIG. 4 is a flow chart that depicts an exemplary embodiment of a method of creating a synthetic projection image.

FIG. 4 is a flow chart that depicts an exemplary embodiment of a method 100 of creating synthetic projection images. Embodiments of the method 100 may be carried out using the imaging system 10 as described above with respect to FIG. 1. The method 100 begins at 102 receiving tomographic projection images. In an exemplary embodiment, the received tomographic projection images are DBT projection images. In another exemplary embodiment, the method includes acquiring the projection images. However in other embodiments, the projection images have been previously acquired and stored. As described above, the DBT projection images are acquired at various positions of the X-ray emitter relative to the patient's breast as depicted in FIG. 2. Also described above, this process is exemplarily carried out by receiving user input commands which are translated into operational instructions and commands from the control unit 32 to the acquisition unit 12 to carry out acquisition of the DBT projection images. In exemplary embodiments, a plurality of projection images are acquired, and in a more specific and non-limiting embodiment, nine projection images are acquired across an acquisition geometry of an arc of about 25°.

As described in further detail herein the method 100 functions to create a synthetic projection image exemplarily from a focal point different from any of the focal points of the positions of the X-ray emitter used to acquire the DBT projection images. As noted above, in an exemplary embodiment, the projection images may be acquired at intervals of roughly 3° apart. An exemplary synthetic projection image may be created for one or more focal points positioned between the focal points of the projection image intervals. In exemplary embodiments as described in further detail herein, this can be used to expand the number of projection images available for 3D reconstruction of the tissue matrix of the imaged object. For example, if an additional synthetic projection image is produced between each of the exemplary nine projection images, this would add an additional eight synthetic projection images for a total of seventeen projection images. If two synthetic projection images were produced between each acquired projection image for a total of sixteen synthetic projection images, this would increase the total to twenty-five projection images. Similarly, if three synthetic projection images were produced between each acquired projection image for a total of twenty-four synthetic projection images and thirty-three total projection images, the total available projection images would be similar to that of an ideal number of projection images while providing higher resolution in the actual acquired projection images.

The method 100 continues at 104 when the image processing unit 36 receives a focal point F for a synthetic projection image. The received focal point F may exemplarily be received through the input device of the imaging system and exemplarily identifies a focal point that is different from any of the focal points or X-ray emitter positions at which the DBT projection images were acquired. Additionally, the received focal point is exemplarily located between the positions of two adjacent acquired DBT projection images. At 106, the image processing unit selects a set of projection images about the received focal point.

In an exemplary embodiment the set of projection images may include at least two projection images. The projection images may include the acquired DBT projection images and/or may include previously created synthetic projection images. In an embodiment as explained in further detail herein, the set of projection images may include all of the available projection images. In one exemplary embodiment, the set of projection images includes a first projection image and a second projection image for the acquired DBT projection images, for example the DBT projection images nearest to or immediately adjacent to the received focal point. In another exemplary embodiment one or both of the first projection image and the second projection image in the set of projection images is a synthetic projection image that is nearest to the received focal point.

Figure 3:
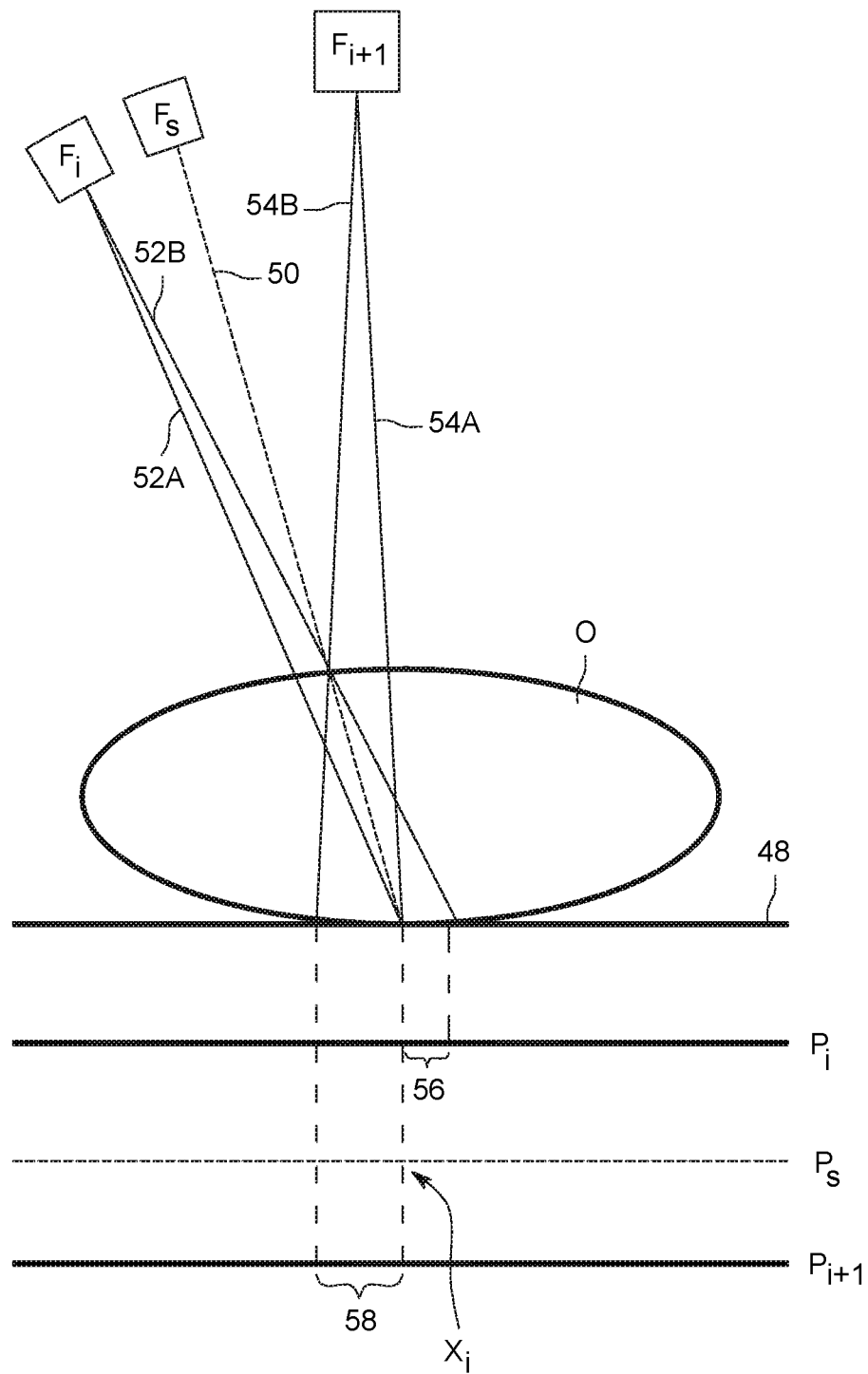
FIG. 3 diagrammatically depicts interpolation of synthetic projection image pixels.

FIG. 3 diagrammatically depicts the interpolation of a synthetic projection image of object O according to the method 100 as described herein. In FIG. 3, the patient's breast O is positioned adjacent the X-ray detector 48. $F_i$ and $F_{i+1}$ represent the X-ray emitter positions respectively used to acquire corresponding DBT projection images $P_i$ and $P_{i+1}$. The received focal point $F_s$ represents an artificial X-ray emitter position located between the positions $F_i$ and $F_{i+1}$ from which the synthetic projection image $P_s$ will be generated. As noted above, while FIG. 4 shows the acquired projection images $P_i$ and $P_{i+1}$ and the synthetic projection image $P_s$ as lines or arrows of pixels, it will be recognized that the actual acquired projection images and synthetic projection images are two dimensional and will constitute a plurality of rows of pixels and that the process as described herein may be repeated across all of the rows of pixels to create a 2D synthetic projection image. In still further exemplary embodiments as described herein, each pixel in the 2D synthetic projection image is processed in parallel.

As depicted in FIG. 4, pixel $X_i$ of the synthetic projection image $P_s$ is the pixel to be created and is represented by the dotted projection line 50 from the focal point $F_s$ through the breast O to the X-ray detector 48. The pixel $X_i$ in the synthetic projection image $P_s$ contains information from all points through the tissue matrix of the breast O along the projection line 50. Respective projection lines 52A and 54 are respectively from focal point $F_i$ and $F_{i+1}$ intersect with projection line 50 where projection line 50 exits the breast O. Similarly, projection lines 52B and 54B respectively from focal point $F_i$ and $F_{i+1}$ intersect projection line 50 at the location where projection line 50 enters the breast O. The points where the projection lines 52A and 52B from focal point $F_i$ hit the detector 48 define the portion 56 of projection image $P_i$ in which information regarding the tissue matrix of the breast O represented in pixel $X_i$ can be found. Similarly, the locations where projection lines 54A and 54B from the focal point $F_{i+1}$ hit the detector 48 define the portion 58 of the projection image $P_{i+1}$ which contains information regarding the tissue matrix of the breast O represented in pixel $X_i$.

Referring back to FIG. 4, the description of which will also refer to FIG. 3 and will focus on an exemplary embodiment in which the set of projection images is made up of a first projection image and a second projection image. It will be recognized from the present disclosure that this process is not so limited and sets of projection images having other numbers of acquired and/or synthetic projection images may be used. At 108 the set of object locations in the projection images $P_i$ and $P_{i+1}$ of the set of projection images that contribute to pixel $X_i$ are identified. These are respectively the portion 56 of a projection image $P_i$ and portion 58 of projection image $P_{i+1}$ identified in FIG. 3. Once these sets of object locations are identified, then pixel candidates from the identified sets of object locations are selected at 110. The selected pixel candidates at 110 represent the best candidate pair of pixels from the projection image $P_i$ and $P_{i+1}$ to represent the information in pixel $X_i$ of the synthetic projection image $P_s$. This can be represented in a general case which is applicable to sets of any number of projection images as:

$$[v] = C(v_i, v_{i+1}) \qquad (1a)$$

While in the specific exemplary core of a set of projection images having two projection images is represented as:

$$v = \operatorname{argmax}_{v \in V} C(v_i, v_{i+1}) \qquad (1b)$$

where V is the set of tissue matrix locations contributing to the value of $X_i$ and $v_i$ is the projection of voxel V on the projection image $P_i$ and $v_{i+1}$ is the projection of voxel V on the acquired projection image $P_{i+1}$.

C is a criterion function for selection of the voxel V of the set of tissue matrix locations contributing to the value of X (e.g. along projection line 50) that is a good candidate for interpolating the value of X. Non-limiting examples of the function C include the following equations:

$$\min(P_i(v_i) - P_{i+1}(v_{i+1})) \quad (2a)$$

$$|Pi(vi) - Pi+1(vi+1)| \quad (2b)$$

$$\left| \frac{P_i(v_i)}{\mu_i} - \frac{P_{i+1}(v_{i+1})}{\mu_{i+1}} \right| \quad (2c)$$

In the above example for function C, a pixel by pixel comparison of the potential pairs of pixels between the pixels of selected portion 56 of $P_i$ and the pixels of selected portion 58 od $P_{i+1}$ is made to find the minimum difference (2a), the minimum absolute difference (2b) or the minimum absolute difference (2c) of the relative intensity of the pixel to the average value of surrounding pixels. The variable μ represents an average value of pixels in the neighborhood of v. These functions, as well as other criterion functions, which may be recognized by a person of ordinary skill in the art, are used to evaluate each of the possible pairs of locations in projection image $P_i$ and projection image $P_{i+1}$ that can be used to interpolate the value of $X_i$ in the synthetic projection image $P_i$. Each of these possible pairs are evaluated to select the pair of pixel candidates that are most likely the best match for interpolation of the value for pixel $X_i$. It will be recognized that in embodiments wherein the set of projection images includes more than two projection images the criteria functions identified above may be further limited with a comparison to a threshold T, in order to select from a subset of the available voxels.

Next at 112 the value for the pixel $X_i$ is calculated from the selected pixel candidates. This calculation is exemplarily represented with:

$$P(X_i) = G(V_i, V_{i+1}) \quad (3)$$

wherein $P_i$ is the synthetic projection image, $X_i$ is the pixel within the synthetic projection image to be interpolated, and G is a fusion operator applied to the selected values for $V_i$ and $V_{+1}$.

The following equations are examples of fusion operators G which may be used in exemplary embodiments of the method.

$$\max(P_i(v_i), P_{i+1}(v_{i+1})) \quad (4a)$$

$$\min(P_i(v_i), P_{i+1}(v_{i+1})) \quad (4b)$$

$$\frac{P_i(v_i) + P_{i+1}(v_{i+1})}{2} \quad (4c)$$

The exemplary embodiments of the fusion operator G identified above disclose exemplary ways in which the values of the pixels in the selected pair of pixel candidates can be combined to calculate the value of a pixel $X_i$ of the synthetic projection $P_s$. The examples identified above exemplarily take the maximum value between the pixels in the pixel pair (4a), the minimum value of the pixels in the pixel pair (4b), or an average of the two values in the pixel pair (4c). It will be recognized that other functions may be used to determine the value of $X_i$ for the synthetic projection image $P_s$.

At 114 the method is used to create each pixel in the synthetic image $X_{i+n}$. In one embodiment, this may be performed by creating each pixel before incrementing to create a next pixel in the synthetic image while in another embodiment all of the pixels in the synthetic projection image are created in parallel. Persons of ordinary skill in the art will recognize that other processing approaches or orders may be used to create each of the pixels in the synthetic image. This process is repeated until a pixel value $X_{i+n}$ is calculated for each pixel in the synthetic projection image $P_s$, as noted above, it is to be remembered that while the diagrammatic representation of FIG. 4 presents the synthetic projection image $P_s$ as a line, it will be recognized that the acquired projection images and the synthetic projection image are two-dimensional and comprise a plurality of rows of pixels rather than a single row as depicted for conciseness in FIG. 4.

At 116 all pixel values $X_{i+n}$ of the pixels in the synthetic projection image are calculated to create a synthetic projection image at 118. As noted above, embodiments disclosed in further detail herein may include a plurality of synthetic projection images and at. 120, after all of the pixels in one synthetic projection image are calculated, the method may be repeated at 120 to calculate a synthetic projection image from a new or additional focal point.

As referenced above, in some embodiments, the set of projection images may include either acquired tomographic projection images, synthetic projection images, or both. In one exemplary embodiment, when a new focal point is received for a synthetic projection image, the selected set of projection images may include the closes available projection images to the received focal point, whether those projection images are acquired tomographic projection images or created synthetic projection images. In an exemplary embodiment, as synthetic projection images are created, those created synthetic projection images may be available and/or used in the creation of further additional synthetic projection images.

The created synthetic projection images 118 can be stored exemplarily at the computer memory 38 associated with the image processing unit, and/or may be presented on the graphical display 42. In still further embodiments, the synthetic projection images as calculated in accordance with the method described above with respect to FIG. 4 may be further used to carry out the additional methods of reconstructing a 3D volume 200 described herein with respect to FIG. 5 or method of creating a synthetic 2D image 300 as described herein with respect to FIG. 6.

Figure 5:
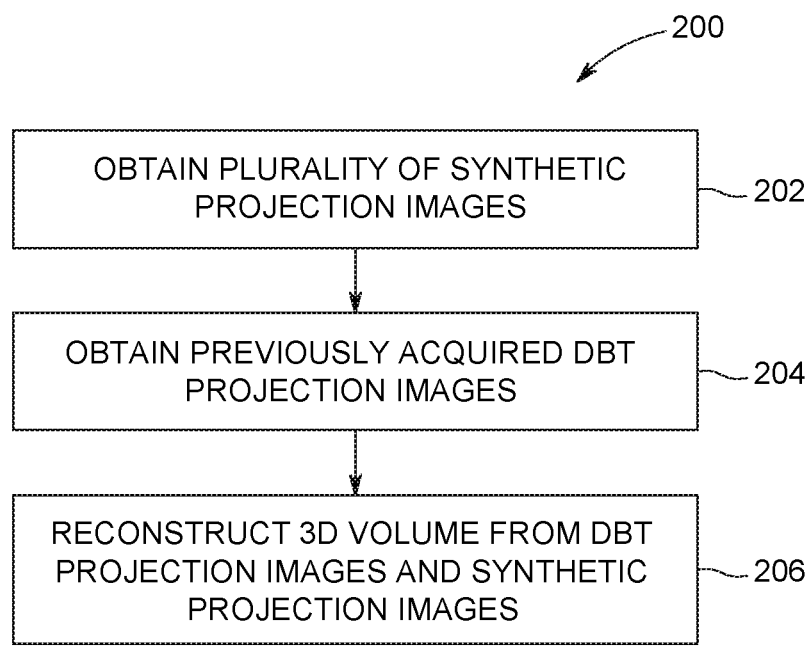
FIG. 5 is a flow chart that depicts an exemplary embodiment of producing a reconstructed 3D volume using synthetic projection images.

FIG. 5 is a flow chart that depicts an exemplary embodiment of a method 200 of reconstructing a 3D volume. It will be recognized that used herein, the phrase "reconstruct a 3D volume or reconstructing an image" is not intended to exclude embodiments of the systems and methods as disclosed herein in which data representing an image or a 3D volume is generated but a viewable representation of such image is not. That being said, it is contemplated that many embodiments disclosed herein generate (or are configured to generate) at least one viewable image.

The method 200 begins by obtaining a plurality of synthetic projection images from a plurality of acquired projection images, exemplarily as described previously with respect to the method 100 in FIG. 4. In non-limiting embodiments, the plurality of synthetic projection images may include one, two, or more synthetic projection images acquired from focal points located between each of the focal points of the acquired projection images. At 204, the previously acquired projection images are obtained. The acquired projection images may exemplarily have been stored in the computer memory associated with the control unit, or elsewhere in an associated imaging system or a picture archiving a communication system (PACS) of a hospital associated with an imaging system. The image processing unit having obtained the previously acquired projection images, which had been used to create the plurality of synthetic projection images, at 206 reconstructs a 3D volume of the tissue matrix of the patient's breast from the DBT projection images and the synthetic projection images. In exemplary embodiments this reconstruction of the 3D volume may be performed using a regularized reconstruction technique. Further non-limiting examples of known reconstruction techniques include filtered back projection (FBP), ordered statistic based back projection, iterative reconstruction, or an adaptive statistical reconstruction.

In an exemplary embodiment, at 206 a regularized reconstruction technique is used to reconstruct the 3D volume. In embodiments, the plurality of synthetic projection images can improve the reconstructed 3D volume image in two ways. First the synthetic projection images provide improved angular sampling resolution of the tissue matrix which more closely approximates an ideal acquisition and the improved angular resolution reduces structural or streaking artifacts in the reconstructed 3D volume image as explained above.

In further exemplary embodiments, the synthetic projection images result in an improved reconstructed 3D volume image during adaptive statistical reconstruction by providing an interpolated intermediate error projection during iterative reconstruction.

In an adaptive statistical reconstruction an estimated reconstruction of the object is compared to a simplified geometrical model resulting in synthesized projections. The synthesized projections and the acquired (measured) projections are both compared to statistical models and object models to result in an updated or refined candidate estimate of the object. These estimated 3D volume images are refined in this manner to iteratively produce the reconstructed 3D volume.

After the 3D volume image is reconstructed, then optionally, the reconstructed 3D volume image may be presented on the graphical display. The reconstructed 3D volume image may also be stored for later access and use in the computer memory 38 of the image processing unit 36.

Figure 6:
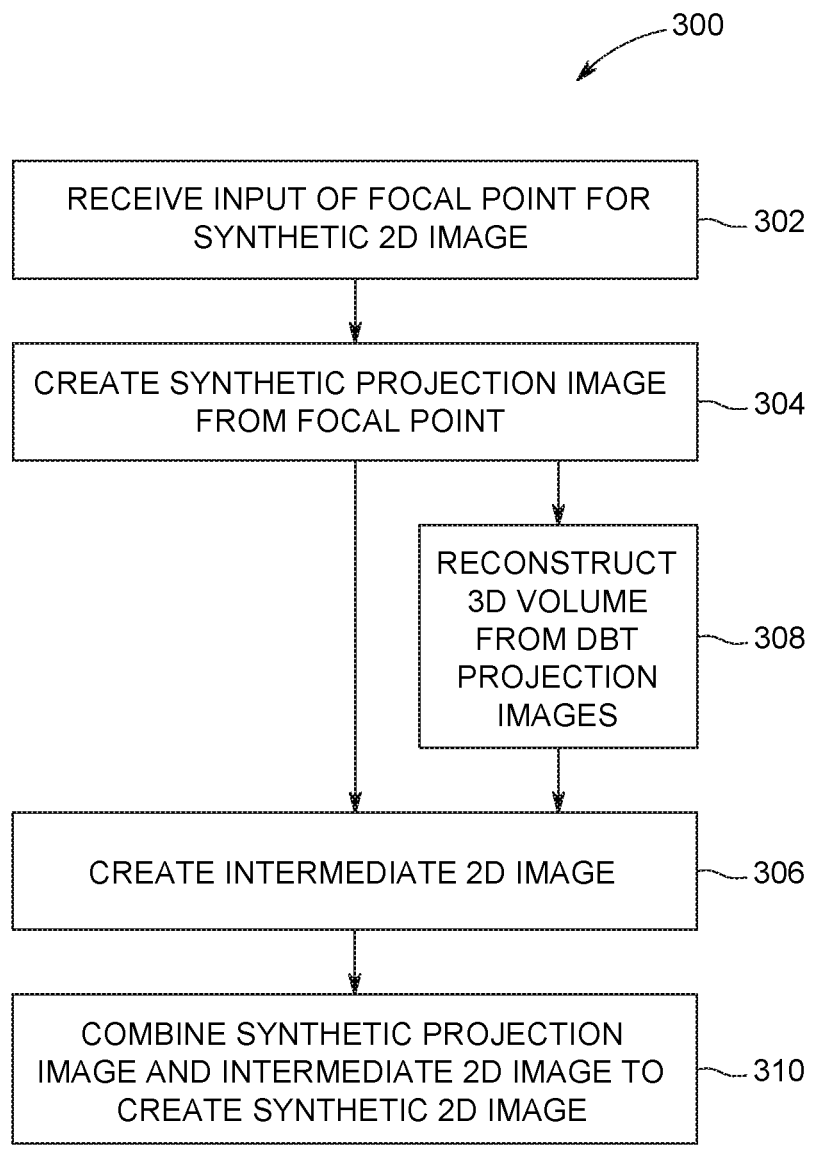
FIG. 6 is a flow chart that depicts an exemplary embodiment of a method of producing a synthetic 2D image from a reconstructed 3D volume.

FIG. 6 is a flow chart that represents an exemplary embodiment of a method 300 of creating a synthetic 2D image from an arbitrary focal point selected by a user. As noted above, it is known in the art to create a 2D image (representative of a full filed digital mammography (FFDM) image) from a DBT 3D reconstruction. The 3D reconstruction is used by selecting one of the original DBT projection images and enhancing that selected DBT projection image with the 3D reconstructed volume image produced from all of the acquired DBT projection images. A similar technique is used in other CT applications, although the typical angular resolution of CT images is far greater than that of the limited number of DBT projection images and comparative low angular resolution in DBT imaging. Therefore, the method 300 presents a solution whereby synthetic 2D image similar to an FFDM image can be produced from any arbitrary focal point selected by a user rather than just those focal points from which a DBT projection image had already been acquired.

At 302 a user input of a focal point for the synthetic 2D image is received. Exemplarily this may be any focal point along the acquisition geometry from the acquisition of the DBT projection images. In other embodiments, this focal point may be independent of acquisition geometry. Exemplarily, the received selected focal point is located between the focal point of two acquired DBT projection images and also is not the same as the focal point at which one of the DBT projection images was acquired.

At 304 a synthetic projection image is created from the user input focal point. Exemplarily, the synthetic projection image is created in accordance with an embodiment of the method 100 described in greater detail above with respect to FIG. 4.

Next, at 306 an intermediate 2D image is created from at least the received focal point for the synthetic projection image. The intermediate 2D image may be created directly from the plurality of projection images.

Optionally, the intermediate 2D image created at 306 may be created from a 3D volume reconstructed from the acquired DBT projection images at 308. A 3D volume can be reconstructed in a variety of known techniques, including but not limited to a regularized reconstruction technique. In one exemplary embodiment, a filter is applied to the acquired 2D projection images so as to obtain filtered projection images of the object. The filter may be of the high-pass type and have a cutoff frequency which may be determined according to the thickness of the object. Reconstruction slicing of the object are then determined. The reconstruction of the slices may include back-projection of the filtered 2D projection images. This exemplary back-projection may in particular embodiments be of the non linear, "ordered statistics based back-projection" type. In linear back-projection, each voxel of the volume is reconstructed using end pixels of information, each pixel being determined by a projection of the voxel into each of the N projections. In non linear back-projection, the maximum intensity pixel among the N is not used, which makes it possible to considerably reduce the replication artifacts caused by the most intense objects. It is to be noted that the reconstruction slices of the object of interest represent the reconstruction volume of the object of interest, creating the reconstructed 3D volume, in such an embodiment, the intermediate 2D image is created at 306 from the reconstructed 3D volume. Exemplarily, this is performed by re-projection of the reconstructed 3D volume or reconstructed slices of the 3D volume in the direction of the received input focal point. This re-projection makes it possible to create the intermediate 2D image of the object of interest. At 310 the synthetic projection image is combined with the intermediate 2D image to create a synthetic 2D image from the user selected focal point. This combination may exemplarily be a linear, pixel to pixel combination.

Finally, the synthetic 2D image from the user input focal point may be presented on the graphical display of the imaging system. Additionally, the image processing system may store the synthetic 2D image on the computer memory associated with the image processing unit. The generation of synthetic 2D images similar to those of FFDM 2D images from an arbitrarily selected user input focal point improves clinician review of DBT imaging results by enabling rendering of enhanced quality 2D images from any focal point of the reconstructed 3D volume, rather than limiting the clinician to only those views already represented by the acquired DBT projection images. This may be particularly helpful during clinician review in the event of super position of tissues which may hide lesions or to more accurately determine the location of a lesion or other object of interest in the medical images.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for medical imaging comprising:
an acquisition unit comprising a radiation source configured to emit X-rays and an X-ray detector configured to receive X-rays having passed through an object to be imaged and produce numerical values representative of the received X-rays, the acquisition unit movable about the object to be imaged to acquire a plurality of projection images, each at a different angle relative to the object to be imaged; and
an image processor that receives an input of a focal point for a synthetic projection image, selects a first projection image and a second projection image adjacent to the focal point from the plurality of projection images, and for each pixel of the synthetic projection image:
identifies a first set of object locations in the first projection image and a second set of object locations in the second projection image that contribute to a pixel of the synthetic projection image; and
calculates a value for the pixel of the synthetic projection image from pixels of the first set of object locations and the second set of object locations;
wherein the image processor creates a synthetic projection image from the calculated values of each pixel of the synthetic projection image.

2. The system of claim 1, further comprising a control unit operatively connected to the acquisition unit, the control unit comprising a processor and computer memory, and the processor operates the acquisition unit to acquire the plurality of projection images and store at the computer memory a position of the radiation source at which each of the plurality of projection images are acquired.

3. The system of claim 1, further comprising a user input device, wherein the image processor receives the input of the focal point for the synthetic projection image from the user input device.

4. The system of claim 1, wherein for each pixel in the synthetic projection image, the image processor selects a first pixel from the first set of object locations and a second pixel from the second set of object locations to form a pixel pair.

5. The system of claim 4, wherein the image processor calculates a value for each pixel of the synthetic projection image from the pixel pair for each pixel in the synthetic projection image.

6. The system of claim 5, wherein the image processor creates a plurality of synthetic projection images from a plurality of focal points, the plurality of projection images comprising a projection image from a focal point located between each of the plurality of projection images acquired with the acquisition unit, and the image processor reconstructs a three dimensional (3D) volume from a combination of the plurality of projection images acquired with the acquisition unit and the plurality of synthetic projection images, and further comprising:
a graphical display operable to visually present the reconstructed 3D volume.

7. The system of claim 5, wherein the image processor reconstructs a 3D volume from at least the plurality of projection images acquired by the acquisition unit, creates an intermediate 2D image from the received focal point for the synthetic projection image from the reconstructed 3D volume, and combines the synthetic projection image with the intermediate two-dimensional (2D) image to create a synthetic 2D image from the received focal point, and further comprising:
a graphical display operable to visually present the reconstructed 3D volume.

8. A method of medical imaging, the method comprising:
receiving a plurality of projection images;
receiving an input of a focal point for a synthetic projection image;
selecting a set of projection images from the plurality of projection images that are adjacent the focal point;
identifying at least a first set of object locations and a second set of object locations in the set of projection images that contribute to a pixel of the synthetic projection image;
calculating a value for the pixel of the synthetic projection image from pixels of the at least first set of object locations and the second set of object locations; and
creating the synthetic projection image from the calculated value of the pixel of the synthetic projection image.

9. The method of claim 8 wherein the set of projection images comprises a first projection image and a second projection image and the first set of object locations are identified in the first projection image and the second set of object locations are identified in the second projection image.

10. The method of claim 8 wherein the set of projection images further comprises at least one synthetic projection image.

11. The method of claim 8, wherein creating a synthetic projection image further comprises calculating a value for each pixel of the synthetic projection image from identified sets of object locations in the first projection image and the second projection image.

12. The method of claim 8, further comprising selecting a first pixel from the first set of object locations and a second pixel from the second set of object locations to form a pixel pair.

13. The method of claim 12, wherein the pixel pairs are selected using at least one of a minimum difference between pixels and a minimum absolute difference between pixels.

14. The method of claim 13, wherein the pixel pairs are further selected using a minimum difference in pixel intensity relative to an average of pixel values of the pixels surrounding the pixels of the pixel pair.

15. The method of claim 12, wherein the pixel value is calculated using at least one of a maximum value between the pixels in the pixel pair, a minimum value between the pixels in the pixel pair, and an average of the values of the pixels in the pixel pair.

16. The method of claim 12, further comprising:
reconstructing a three-dimensional (3D) volume from a combination of the plurality of projection images acquired with the acquisition unit and at least one synthetic projection image.

17. The method of claim 16, further comprising:
creating a plurality of synthetic projection images from a plurality of received focal points, at least one focal point of the plurality of received focal points located between each of the plurality of projection images acquired with the acquisition unit;
wherein the 3D volume is reconstructed using the plurality of synthetic projection images.

18. The method of claim 8, further comprising:
creating a synthetic two-dimensional (2D) image from the received focal point for the synthetic projection image, and the synthetic projection image.

19. The method of claim 18 further comprising:
reconstructing a 3D volume from at least the plurality of projection images;
creating an intermediate 2D image from the received focal point for the synthetic projection image from the reconstructed 3D volume.

20. The method of claim 19, wherein reconstructing the 3D volume comprises using a regularized reconstruction technique and creating the intermediate 2D image comprises re-projecting the 3D volume from the received focal point.

21. The method of claim 19, further comprising combining the intermediate 2D image with the synthetic projection image to create the synthetic 2D image.

22. The method of claim 18, further comprising:
creating an intermediate 2D image from the plurality of projection images; and
combining the intermediate 2D image with the synthetic projection image to create the synthetic 2D image.

* * * * *